United States Patent [19]

Shera

[11] Patent Number: 5,209,834
[45] Date of Patent: May 11, 1993

[54] ORDERED TRANSPORT AND IDENTIFICATION OF PARTICLES

[75] Inventor: E. Brooks Shera, Los Alamos, N. Mex.

[73] Assignee: The United States of America as represented by the United States Department of Energy, Washington, D.C.

[21] Appl. No.: 848,582

[22] Filed: Mar. 9, 1992

[51] Int. Cl.[5] ............... G01N 27/26; G01N 27/447
[52] U.S. Cl. ........................... 204/183.3; 204/180.1; 204/299 R
[58] Field of Search ............. 204/299 R, 180.1, 183.3

[56] References Cited

U.S. PATENT DOCUMENTS 4,793,705  12/1988  Shera .................................. 356/318
4,962,037  10/1990  Shera et al. ...................... 436/501 X

OTHER PUBLICATIONS

James W. Jorgenson and Krynn DeArman Lukacs, "Capillary Zone Electrophoresis", Science, vol. 222, pp. 266-272.
James W. Jorgenson and Krynn DeAmar Lukacs, "Zone Electrophoresis in Open-Tubular Glass Capillaries" Analytical Chemistry, 53, pp. 1298-1302.
C. L. Rice and R. Whitehead, "Electrokinetic Flow in a Narrow Cylindrical Capillary," Journal of Physical Chemistry 69, pp. 4017-4023.
E. Brooks Shera et al., "Detection of Single Fluorescent Molecules", Chemical Physics Letters, vol. 1-4, No. 6, pp. 553-557.

Primary Examiner—John Niebling
Assistant Examiner—John S. Starsiak, Jr.
Attorney, Agent, or Firm—Ray G. Wilson; Paul D. Gaetjens; William R. Moser

[57] ABSTRACT

A method and apparatus are provided for application of electrical field gradients to induce particle velocities to enable particle sequence and identification information to be obtained. Particle sequence is maintained by providing electroosmotic flow for an electrolytic solution in a particle transport tube. The transport tube and electrolytic solution are selected to provide an electroosmotic radius of >100 so that a plug flow profile is obtained for the electrolytic solution in the transport tube. Thus, particles are maintained in the same order in which they are introduced in the transport tube. When the particles also have known electrophoretic velocities, the field gradients introduce an electrophoretic velocity component onto the electroosmotic velocity. The time that the particles pass selected locations along the transport tube may then be detected and the electrophoretic velocity component calculated for particle identification. One particular application is the ordered transport and identification of labeled nucleotides sequentially cleaved from a strand of DNA.

9 Claims, 3 Drawing Sheets

ORDERED TRANSPORT AND IDENTIFICATION OF PARTICLES

This invention is the result of a contract with the Department of Energy (Contract No. W-7405-ENG-36).

BACKGROUND OF THE INVENTION

This invention relates to electrokinetic flow and, more particularly, to the use of electrokinetic flow to transport particles.

When a liquid flows slowly through a cylindrical tube, propelled by gravity or by an applied pressure difference between the ends of the tube, a parabolic laminar (Poiseuille) flow velocity profile is established transverse to the direction of flow. The flow velocity is a maximum along the central axis of the tube and approaches zero at the tube wall. When such a moving liquid is used to transport particles from one location to another, the particles will have a range of transit times that depends upon their radial distance from the tube axis. Particles near the tube axis will travel faster and may overtake particles traveling near the wall, thereby scrambling the order of the transported particles. Moreover, small particles or molecules released into the stream will diffuse radially across zones of different velocity in an unpredictable fashion. Thus, even if such particles start their travel at the same point in the tube and at the same time, they will arrive at the end of the tube at different and unpredictable times.

The inability of a flow stream with a Poiseuille flow velocity profile to deliver small particles or molecules (all referred to herein as particles) in a predictable manner presents a serious problem for applications that require particles to arrive at the far end of a transport tube after a predictable transit time or in a predictable order. For example, a method for sequencing DNA, described in U.S. Pat. No. 4,962,037, requires that individual DNA bases be transported via a flow stream from a zone in which enzymatic cleavage is occurring into a DNA base detector. The individual bases must arrive at the detector in a known sequence so that the DNA sequence can be reconstructed. Sequence errors can be avoided by reducing the number of bases in the transport flow stream, but only at the cost of a major reduction in sequencing rate.

In another aspect of particle sequencing and identification, particles are individually tagged with fluorescent labels (dye molecules that emit a characteristic fluorescence when excited with a corresponding laser). Different dyes are required to identify individual ones of the particles with a concomitant capability to excite and detect fluorescence from the various dyes. It would be desirable to provide only a single dye for use in identifying particular particle species.

These problems are addressed by the present invention wherein electrokinetic flow is used for particle transport. Electrokinetic flow includes an electroosmotic flow component for maintaining a continuous ordered flow of particles and an electrophoretic flow component for providing a velocity differential that uniquely identifies the particles by species.

Accordingly, it is an object of the present invention to provide a flow stream capable of maintaining an ordered stream of small particles and/or molecules.

It is another object of the present invention to maintain a plug flow profile across a capillary tube and along the length of the capillary tube.

Yet another object of the present invention is to provide a predictable electroosmotic flow rate to calculate an electrophoretic velocity from a measured total particle flow rate for use in particle identification.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention may comprise means for the ordered transport of particles. A transport tube, a high voltage means for applying an electrical field gradient along the transport tube, and an electrolytic solution for moving within the transport tube provide for transporting the particles. The transport tube and electrolytic solution cooperate to establish an electric double layer for electroosmotic flow of the electrolytic solution under the electrical field, wherein the electrolytic solution and the transport tube are effective to obtain an electroosmotic radius of at least a value of about 100 to provide a plug flow velocity profile of the electrolytic solution to maintain the particles in an ordered sequence during transport through the transport tube. In another characterization of the present invention, a particle transport means includes a transport tube and electrolytic solution effective to obtain an electroosmotic radius greater than a value of about 100 to provide a plug flow velocity profile of the electrolytic solution in the tube. Particle detector means are spaced along the axis of the tube in a region of electroosmotic flow so that electrokinetic particle velocity can be measured. From the measured particle velocity and known electroosmotic velocity of the electrolyte, the particle electrophoretic velocity can be calculated for particle identification.

In yet another characterization, a method for establishing the identity of particles having known electrophoretic velocities enables particles to be continuously input to an electrolyte supporting a predetermined electrical field gradient within a particle transport tube. Particle detector means measures the time of passage of the particles at known locations along the transport to provide a measure of the electrophoretic velocity of each particle from which the particle can be identified.

In a particular application, the particles are fluorescently labeled nucleotide molecules from a DNA strand that is being sequenced and the molecules are identified from differences in the calculated electrophoretic velocities.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION OF THE INVENTION

Figure 1:
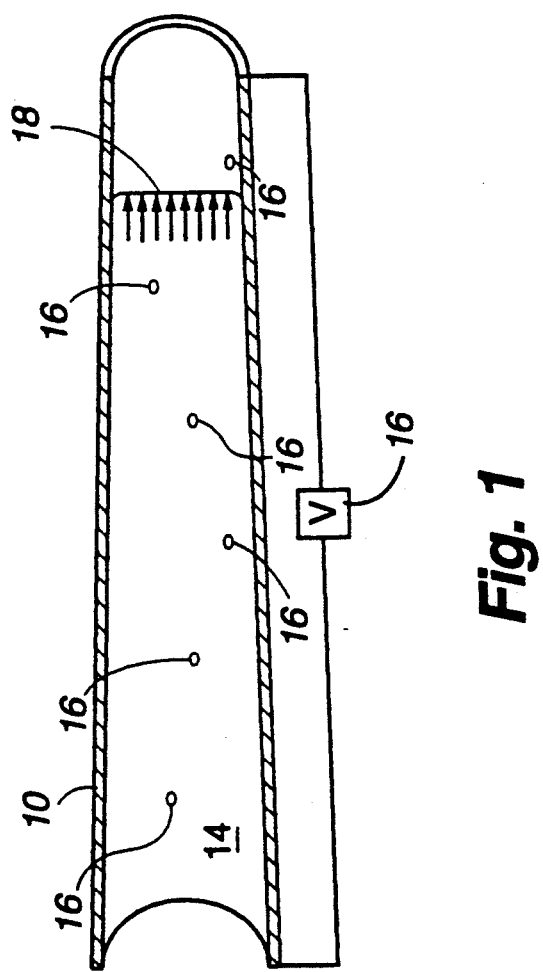
FIG. 1 is a pictorial illustration of an electro-osmotic flow device according to one embodiment of the present invention.

Referring first to FIG. 1, the present invention provides an ordered transportation of small particles through a capillary tube using electroosmotic flow to transport the particles. As used herein, the term "particle" refers to particles of any size, but particularly to very small particles subject to random transverse movements and to molecules where the sequence of the molecules is important. A large electroosmotic radius is provided wherein a plug flow is developed substantially across the diameter of the capillary so that individual particle velocities are predictable for determining the arrival sequence of the particles.

In practicing the invention, the particles to be transported are placed in an electrolytic solution that fills a transport tube. The walls of the transport tube are composed of a material, or treated with a substance, that establishes an electric double layer when in contact with the electrolyte. An electrical potential difference is applied between the ends of the transport tube, with a polarity determined by the electric double layer effective to produce electroosmotic flow in the desired direction through the tube. An external pressure difference might be applied between the ends of the transport tube to correct for inertial distortion of the flow profile that occurs when the diameter of the tube is not constant throughout its length.

To establish electroosmotic flow, as shown in FIG. 1, an electrolyte 14 is placed inside a capillary tube 10 having an inner wall material that becomes charged through contact with the electrolyte. A suitable wall material, e.g., a monomolecular polymeric layer as described in U.S. Pat. No. 4,680,201, issued Jul. 14, 1987, incorporated herein by reference, becomes charged either through the ionization of surface groups on the capillary walls or through adsorption of charged species from the electrolyte onto the inner surface. The electrolyte within the capillary is then no longer neutral, but acquires a net charge and an interfacial electric double layer is formed at the capillary wall/electrolyte interface. Under the action of an electric field 12 applied parallel to the interface, the electrolyte 14 moves parallel to the interface in the direction determined by the charge species in the electrolyte 14 and the direction of the applied field 12. Particles 16 located in the electrolyte 14 are transported with the electrolyte 14 along the transport capillary tube 10. As hereinafter shown, selection of an electrolyte 14 with material forming the wall of tube 10 provides a uniform radial velocity (plug flow) profile 18 so that particles 16 will have a constant electroosmotic velocity regardless of the radial location of a particle 16 within tube 10.

It is shown in C. L. Rice et al., "Electrokinetic Flow in a Narrow Cylindrical Capillary," 69 J. Phys. Chem., No. 11, pp 4017-4023, that the electrolyte electroosmotic velocity profile as a function of radius from the capillary tube axis under conditions of no applied pressure gradient can be represented as:

$$v_z(r) = -\Omega E_z \left[ 1 - \frac{I_o(\kappa r)}{I_o(\kappa a)} \right] \quad (1)$$

where $\epsilon$ is the dielectric constant of the electrolyte;

$\psi_o$ is the capillary wall potential;

$\eta$ is the electrolyte coefficient of viscosity;

$\kappa$ is the reciprocal of the Debye length, i.e., reciprocal of the double-layer thickness;

$I_o$ is the zero-order modified Bessel function of the first kind;

r is a radial distance from the capillary tube axis;

a is the radius of the capillary tube.

Figure 2:
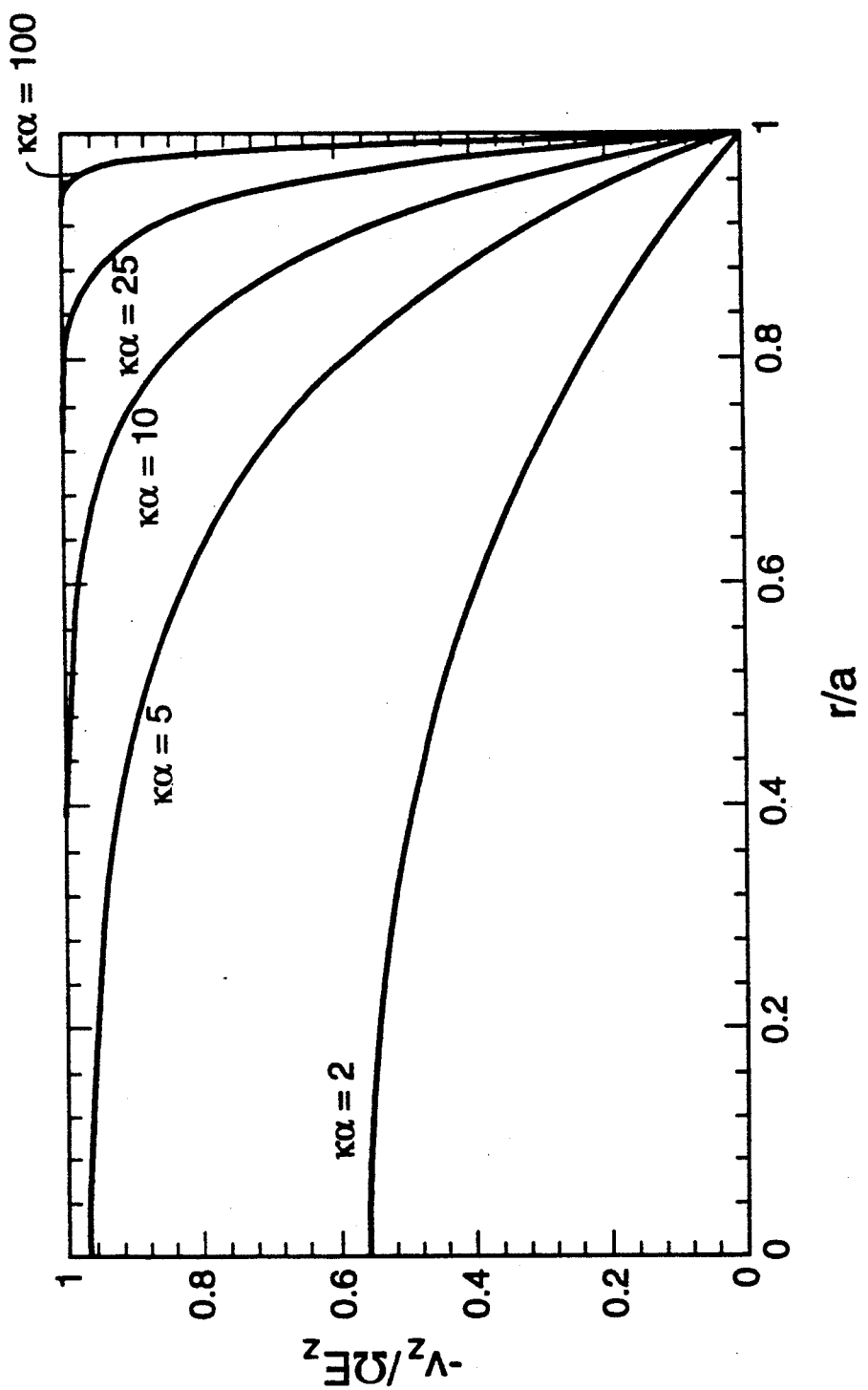
FIG. 2 graphically depicts the electroosmotic flow profile at various electroosmotic radii.

The function $[1-(I_o(\text{``}r\text{''}))/I_o(\kappa a)]$ is shown graphically in FIG. 2 to show velocity profiles for various values of electroosmotic radius $\kappa a$. In accordance with the present invention, the electroosmotic radius is very large, i.e., $\kappa a > 100$ so that $(I_o(\kappa r)/I_o(\kappa a))$ is very small and a plug flow profile $(v_z(r) < 0.992\, v_z(0))$ exists for $0 < r < 0.95\, a$.

Thus, the present invention operates to achieve a uniform and predictable transit time and predictable arrival order by eliminating the non-uniform radial velocity profile that characterizes normal pressure-induced flow. Electroosmotic plug flow, as hereinabove described, has a uniform radial velocity profile except for a very narrow region near the capillary tube wall. Particles transported by the electrolyte will therefore have a constant transit time, substantially independent of their radial position in the tube. The ordering of a sequence of particles released into the flow stream is not changed by the transport process.

In one particular experimental embodiment, transport tube 10 was a 155 μm silica fiber capillary tube and electrolyte 14 was a TRIS buffer solution of pH 10. High voltage power supply 12 provided a voltage difference in the range of 1000-2000 volts with the positive terminal connected to the supply end of tube 10. The electrolyte flow was toward the negative terminal. A current flow of 1.5 μA was obtained during electrolyte flow. The electroosmotic radius of the tube was about 7500 and good plug flow was observed.

In some applications, a tapered capillary tube is desired to focus the flow stream. When the potential difference is applied across the entire length of the capillary tube, the plug flow profile is generally maintained in spite of variations in tube diameter. A decrease in tubing diameter results in an increase in the voltage gradient, which produces an increase in the electroosmotic flow velocity that is sufficient to keep constant the volume of fluid driven through each section of tube, independent of diameter. Even with a taper or tube radius as small as 1 μm, the electroosmotic radius remains above 100 for a silica fiber capillary and the TRIS electrolyte described above.

If the tube diameter changes are abrupt rather than a uniform taper there may be some inertial distortion of the plug flow since an abrupt decrease in diameter makes the fluid near the wall temporarily travel faster than the fluid near the tube center. It will be appreciated that this distortion of plug flow can be minimized by applying an appropriate external pressure difference between the ends of the tube to induce a compensating amount of Poiseuille flow.

In some instances, variations in transport times arising from electrophoretic effects can occur between different particles. These variations can be advantageously used to distinguish individual molecules where the velocity due to electrophoretic migration is known.

In one particular application, U.S. Pat. No. 4,962,037 to Jett et al. teaches a process for sequencing genomic DNA by sequentially cleaving individual bases from a DNA strand and detecting the fluorescence of individual fluorescent labels that have been applied to each base type. The detection of individual bases is reported in Shera et al., "Detection of Single Fluorescent Molecules," 174 Chem. Phys. Letters, No. 6, pp. 553-557 (1990), incorporated by reference. As taught by Jett et al, four different and distinguishable label dyes are required to identify the four bases. However, Gross et al., "Indirect Fluorimetric Detection and Quantification in Capillary Zone Electrophoresis of Inorganic Anions and Nucleotides," 480 J. Chromatography, pp. 169-178 (1989), shows that capillary zone electrophoresis can be used to separate a sample containing nucleotides forming DNA, i.e., the bases adenosine, guanosine, cytidiene, and thymidine, into zones of the individual nucleotides. This result indicates a difference in electrophoretic speeds between the individual nucleotides.

In one aspect of the present invention, the electrophoretic and electroosmotic processes, hereinafter collectively called electrokinetic processes, are used to identify the individual bases in a sequence string. Only a single fluorescent label is now needed for the sole purpose of indicating the passage of a nucleotide through a detector. Identification of individual nucleotides is accomplished by determining the electrokinetic velocity of each molecule in the sequence of molecules.

Figure 3:
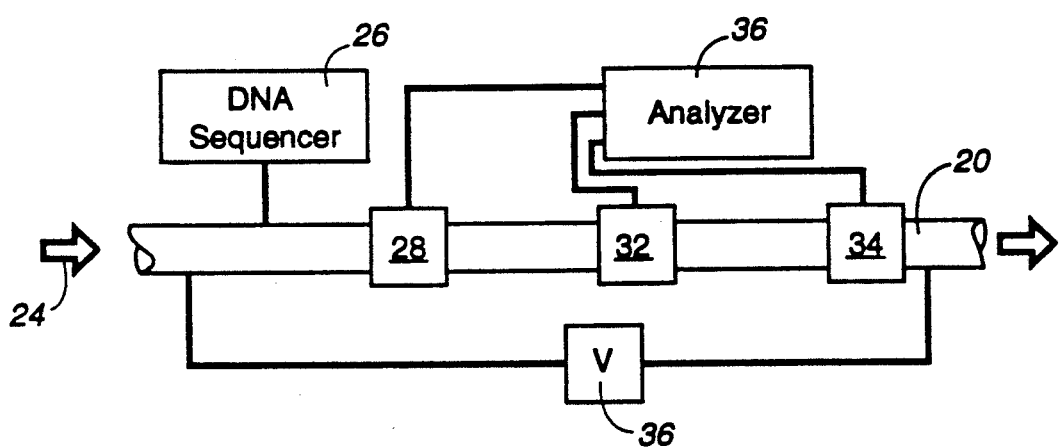
FIG. 3 is a pictorial illustration of an electrokinetic sequence detector according to one embodiment of the present invention.

An embodiment of an electrokinetic sequence detector is shown in FIG. 3. Electrokinetic flow tube 20 has an electrolyte 24 flowing through tube 20 and is connected to DNA suspension and degradation apparatus 26 (see U.S. Pat. No. 4,962,037) for providing a sequence of DNA nucleotides within flowing electrolyte 26. A suitable exonuclease may be contained within apparatus 26 or provided within electrolyte 24 for sequentially cleaving fluorescently labeled nucleotides from a DNA sequence being investigated. A high voltage 22 is applied along capillary tube 20 to establish a desired electroosmotic flow rate within capillary tube 20 and to provide a potential gradient for electrophoretic movement of the nucleotides.

Two or more single molecule detectors 28, 32, and 34 are provided along capillary tube 20, where the flow detectors may be provided as taught by Shera ibid. The electrokinetic velocity of the nucleotides is determined by their transit time between detectors 28 and 32 and/or 34 that are spatially separated along the axis of capillary tube 20. Only two of detectors 28, 32, and 34 are needed for velocity determination, but a third detector provides some redundancy and ambiguity resolution re multiple-molecules, as hereinafter discussed.

Alternatively, a section of tube 20 can be illuminated and optically imaged onto a sensitive detector, such as a charge coupled plate. An image tracking procedure such as described in U.S. Pat. No. 4,793,703, to Shera, then enables unambiguous determination of particle velocities to be made. An appropriate tracking procedure allows several particles to be individually tracked along an illuminated portion of tube 20.

The time of passage of the particles is detected by the detectors and provided to analyzer 36 for identification of the nucleotides moving along capillary 20. The electroosmotic radius of capillary 20 is very large, as discussed above for Figure so that electrolyte 24 provides a plug flow to maintain the order of the nucleotides within capillary 20. From the measured electrokinetic flow rate and the known electroosmotic flow rate, the electrophoretic velocity component can be readily calculated for use in nucleotide identification.

In the simplest form, only one particle or nucleotide is in a region between detectors at a given time, thereby avoiding timing ambiguity that might be caused by the presence of several molecules simultaneously. However, if the sequence consists of only a small number of components, each with a characteristic electrokinetic velocity, the identity of each passing molecule can be readily determined from the observed time differences even when several molecules are simultaneously in transit between detectors. Additional detectors located at other points along the column can further resolve multiple-molecule ambiguities, if necessary. The ability to process several molecules simultaneously is important if a high analysis rate is needed.

The apparatus shown in FIG. 3 may be used with any particles having known electrophoretic velocities and with or without electroosmotic movement of the electrolyte 24. In all events, a continuous particle identification device is provided using the principles of electrophoresis rather than the batch processing of conventional electrophoresis analysis devices. In some applications, the only particle velocity may be its electrophoretic velocity. In other applications, electrolyte 24 may have a pressure induced velocity so that the total measured particle velocity contains velocity components from both the movement of electrolyte 24 and electrophoretic effects. The capability for continuous particle identification may have particular application to, e.g., the monitoring of continuous chemical processes.

The foregoing description of embodiment of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for determining the identity of particles having known electrophoretic velocities, comprising the steps of:

establishing an electroosmotic flow rate of an electrolytic solution in a transport tube where said electrolytic solution and said transport tube are effective to obtain an electroosmotic radius of at least 100 to provide a plug flow velocity profile of said electrolytic solution in said transport tube;

introducing said particles into said flow of said electrolytic solution;

detecting the passage of each one of said particles along said transport tube to provide a measure of the electrokinetic velocity of each one of said particles; and determining the electrophoretic velocity of each one of said particles from said measured electrokinetic velocity of each one of said particles and said electroosmotic flow rate, said electrophoretic velocity serving to identify each one of said particles.

2. A method according to claim 1, wherein said particles are individual molecules of fluorescently labeled nucleotides from DNA.

3. A method for determining the identity of particles having known electrophoretic velocities, comprising the steps of:
   establishing a predetermined electrical field gradient along a electrolytic solution in a transport tube;
   introducing each one of said particles sequentially into said electrolytic solution;
   detecting the time of passage of each one of said particles along said transport tube to provide a measured velocity that is functionally related to the electrophoretic velocity of each one of said particles.

4. A method according to claim 3, further including the steps of:
   providing said electrolytic solution with a known velocity; and
   calculating the electrophoretic velocity of each one of said particles from said known velocity and said measured velocity.

5. A method according to claim 4, wherein the step of providing said electrolytic solution with a known velocity further includes the step of:
   establishing an electroosmotic flow of said electrolytic solution in said transport tube wherein said electrolytic solution and said transport tube are effective to obtain an electroosmotic radius greater than a value of about 100 to provide a plug flow velocity profile of said electrolytic solution in said transport tube.

6. Apparatus for an ordered transport of particles for analysis, comprising:
   a particle transport tube that is tapered to provide a focused flow of said electrolytic solution for said particles;
   high voltage means for applying an electrical field gradient along said transport tube; and
   an electrolytic solution for moving within said transport tube for transporting said particles, said electrolyte functionally cooperating with said transport tube to establish an electric double layer for electroosmotic flow of said electrolytic solution under said electrical field, wherein said electrolytic solution and said transport tube are effective to obtain an electroosmotic radius greater than a value of about 100 to provide a plug flow velocity profile in an ordered sequence during transport through said transport tube.

7. Apparatus according to claim 1, further including means for introducing into said electrolytic solution molecules of fluorescently labeled nucleotides from DNA.

8. Apparatus according to claim 1, further including:
   particle detector means spaced along said transport tube in a region of said electroosmotic flow and outputting a plurality of electrical signals indicative of passage of each one of said particles through said transport tube; and
   analyzer means receiving said electrical signals for determining the electrophoretic velocity of each of said particles long said transport tube to identify each of said particles.

9. Apparatus according to claim 5, further including means for introducing into said electrolytic solution molecules of fluorescently labeled nucleotides from DNA.

* * * * *